US00PP14067P39

(12) United States Plant Patent
Noodelijk

(10) Patent No.: US PP14,067 P3
(45) Date of Patent: Aug. 19, 2003

(54) CHRYSANTHEMUM PLANT NAMED 'RESOLUTE'

(75) Inventor: Robert Noodelijk, Woubrugge (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 09/757,641

(22) Filed: Jan. 11, 2001

(65) Prior Publication Data

US 2002/0092062 P1 Jul. 11, 2002

(51) Int. Cl.[7] ..... A01H 5/00

(52) U.S. Cl. ..... Plt./288

(58) Field of Search ..... Plt./288

*Primary Examiner*—Bruce R. Campell
*Assistant Examiner*—Anne Marie Grünberg
(74) *Attorney, Agent, or Firm*—Parkhurst & Wendel, L.L.P.

(57) ABSTRACT

A Chrysanthemum plant named 'RESOLUTE' characterized by its large sized blooms with white ray-florets and green disc florets.

3 Drawing Sheets

BACKGROUND OF THE INVENTION

'RESOLUTE' is a product of a breeding-program that had the objective of creating new chrysanthemum cultivars with a decorative type flower, a 7 week response and a medium plant height. The new plant of the present invention comprises a new and distinct cultivar of Chrysanthemum plant. 'RESOLUTE' is a seedling from a cross in a breeding program maintained under the control of inventor. The female parent is # 93.0202 -unpatented-, an unamed seedling not available to inventor for description. The male parent is unknown, being a mixed population of a group of male parents. The new and distinct cultivar was discovered and selected as a flowering plant within the progeny of the stated cross by Rob Noodelijk in a controlled environment (greenhouse) in Rijsenhout, Holland in September, 1998. The first act of asexual reproduction of 'RESOLUTE' was accomplished when vegetative cuttings were taken from the initial selection in November, 1998 in a controlled environment in Rijsenhout, Holland.

SUMMARY OF THE INVENTION

The present invention is a new and distinct variety of chrysanthemum bearing large sized blooms with white ray-florets and green disc florets (only visible when mature).

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
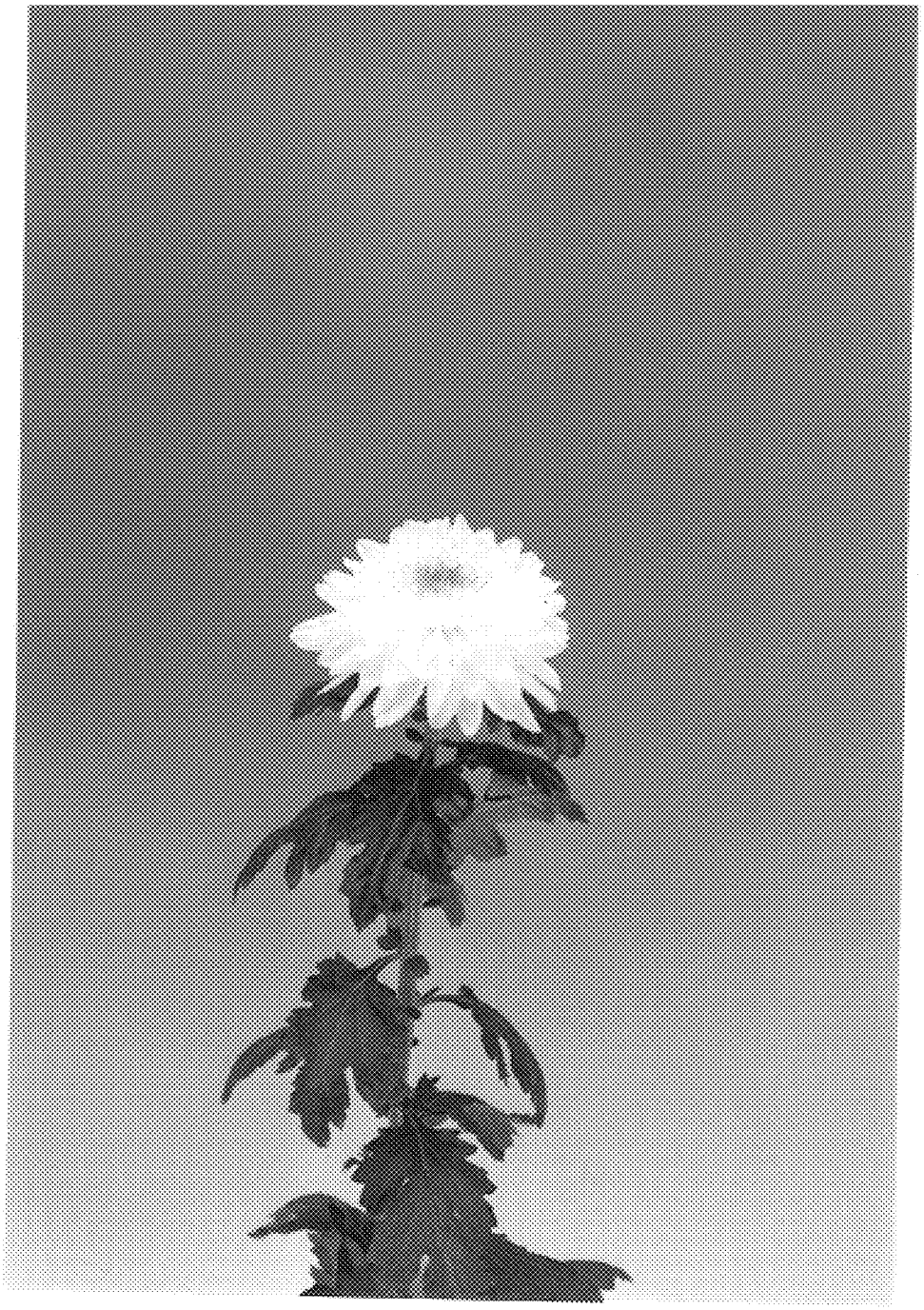
FIG. 1 shows a plant of the cultivar in full bloom.
Figure 2:
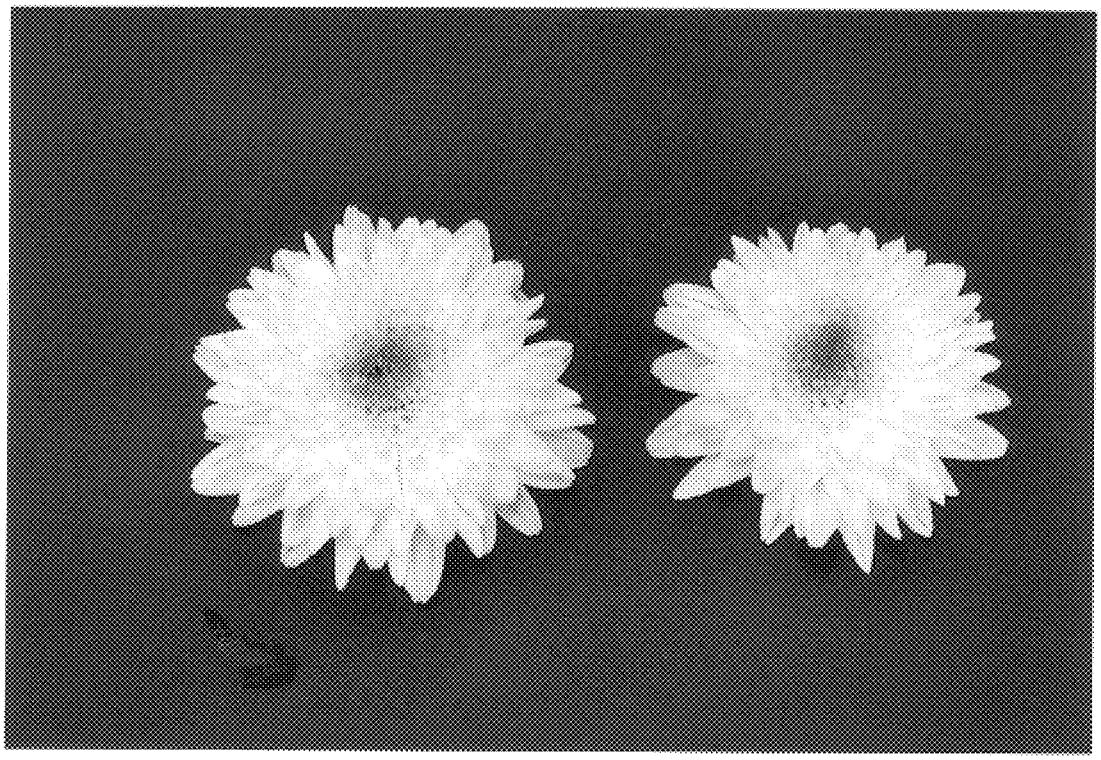
FIG. 2 shows the various stages of bloom of the new cultivar.
Figure 3:
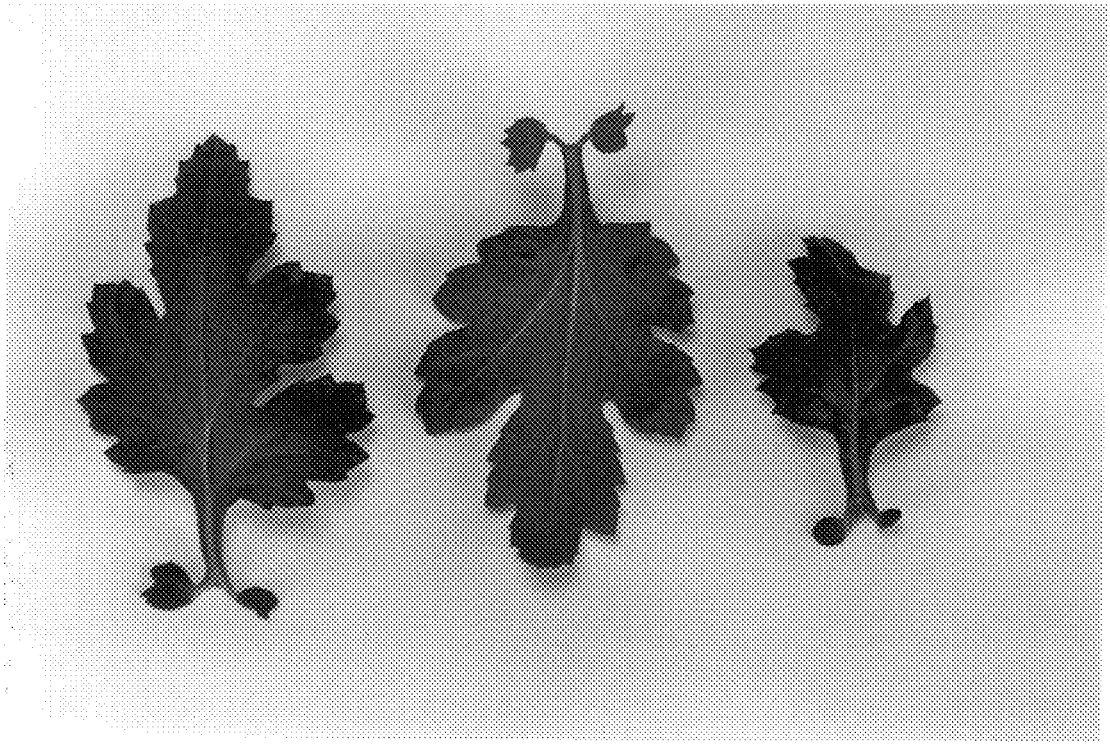
FIG. 3 shows the foliage of the new cultivar.

This new variety of chrysanthemum is of the botanical classification Chrysanthemum morifolium. The observations and measurements were gathered from plants grown in April/May in a greenhouse in Rijsenhout, Holland in a photo-periodic controlled crop under conditions generally used in commercial practice. The greenhouse temperatures during this crop were at day-time between 18° C. and 25° C. and at night 20° C. After a long day period of 14 days, the photo-periodic response time in this crop was 50 days. After the long day period to flowering, growth retardants were applied 2 to 3 times in an average dose of 2.5 gram/liter water. The plants were observed (directly) during the flowering of this crop. No tests were done on disease or insect resistance or susceptibility. No tests were done on cold or drought tolerance. This new variety produces large sized blooms with white ray-florets and green disc-florets blooming on the plant for 5 weeks. This new variety of chrysanthemum has been found to retain its distinctive characteristics throughout successive propagations; however, the phenotype may vary significantly with variations in environment such as light intensity and temperature. To show the phenotype as described, 'RESOLUTE' can be planted without assimilation lightning (high pressure sodium lamps) between week 50 and week 40 of the next year under greenhouse conditions in Holland. With assimilation light (minimum level 2500 lux) it can be planted year round under greenhouse conditions in Holland.

From the cultivars known to inventor, the most similar existing cultivar in comparison to 'Resolute' is 'Rebonnet'. When 'Rebonnet' and 'Resolute' are being compared the following differences are noticed: The difference of 'Rebonnet' and 'Resolute' are; (1) flower color. The flower of 'Rebonnet' is completely pure white. 'Resolute' has a yellow-green center. (2) Growth rate. 'Rebonnet' has a vigorous growth rate, 'Resolute' has a moderate growth rate.

The following is a description of the plant and characteristics that distinguish 'RESOLUTE' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, 1995 edition.

Botanical Description of Cultivar 'Resolute'

Bud:

*Size.*—Large; cross section 1.4 cm, height 1.2 cm.
*Outside color.*—White 155 A.
*Involucral bracts.*—2 rows, length 9 mm, width 4 mm.
*Involucral bracts among disc-florets.*—Not present.
*Involucral bracts color.*—Green 137 A.

Bloom:

*Type.*—Decorative.
*Height.*—High, 5.0 cm.
*Size.*—Large.
*Fully expanded.*—9.5 cm.
*Number of blooms per stem.*—Not applicable.
*Performance on the plant.*—21 days.
*Seeds if crossed.*—Produced in small quantities oval shaped grey-brown 199 A, 2 mm in length.
*Fragrance.*—Typical chrysanthemum, slight.

Color:

*Center of the flower* (*disc-florets*).—Immature yellow-green 145 A. Mature yellow-green 146 A.
*Color of upper surface of the ray-florets*.—White 155 A.
*Color of the lower surface of the ray-florets*.—White 155 A.
*Tonality from distance.*—A disbudded mum with white flowers and a green disc.
*Color of the upper surface of the ray-florets after aging of the plant.*—White 155 A.

Ray florets:

*Texture.*—Upper and under side smooth.
*Number.*—170–180.
*Cross-section.*—Concave.
*Longitudinal axis of majority.*—Straight to incurved.
*Length of corolla tube.*—Medium, 1.0–1.3 cm.
*Ray-floret margin.*—Entire.
*Ray-floret length.*—4.5–5.0 cm.
*Ray-floret width.*—0.9–1.2 cm.
*Ratio length/width.*—High.
*Shape of tip.*—Rounded.

Disc florets:

*Disc diameter.*—0.7 cm.
*Distribution of disc florets.*—Numerous visible at a mature stage of flowering.
*Shape.*—Tubular.
*Color.*—Yellow-green 145 A.
*Receptacle shape.*—Conical raised.

Reproductive organs:

*Stamen* (*present in disc florets only*).—Thin, 3 mm length.
*Number of stamen.*—4.
*Stamen color.*—Yellow-green 144 A.
*Pollen.*—Not present.
*Styles* (*present in both ray and disc florets*).—Thin.
*Style color.*—Yellow-green 144 A.
*Style length.*—4 mm.
*Stigmas color.*—Yellow-green 144 A.
*Stigma width.*—1 mm.
*Ovaries.*—Enclosed in calyx.

Plant:

*Form.*—A disbudded mum meant for erect culture.
*Growth habit.*—Upright.
*Growth rate.*—Moderate.
*Height.*—100 cm.
*Internodes.*—2 cm.
*Spray formation.*—Not applicable; not grown as a spray mum.
*Stem color.*—Green 137 A.
*Stem strength.*—Strong.
*Stem brittleness.*—Present.
*Stem anthocyanin coloration.*—Absent.
*Peduncle length.*—3.5–4.0 cm.
*Peduncle color.*—Green 137 A.
*Flowering response* (*photo-periodic controlled crop, not natural season*).—50 days.

Foliage:

*Color mature.*—Upper side green 137 A. Under side green 137 B.
*Color immature.*—Upper side green 137 C. Under side green 137 D.
*Size.*—Large; length 9 cm, width 6 cm.
*Quantity* (*number per single stem*).—32–35.
*Shape.*—Ovate.
*Texture upper side.*—Fleshy and glabrous.
*Texture under side.*—Pubescent.
*Venation arrangement.*—Palmate.
*Shape of the margin.*—Crenated.
*Shape of base of sinus between lateral lobes.*—Acute.
*Margin of sinus between lateral lobes.*—Converging.
*Shape of base.*—Truncate.
*Apex.*—Cuspidate.
*Petiole length.*—1.5–3 cm.
*Petiole color.*—Green 137 A.

Differences with the comparison Varieties

| | 'Resolute' | 'Rebonnet' |
|---|---|---|
| Color of the center of the flower | Yellow-green 146 A | White 155 D |
| Color of the upper side of the ray-florets | White 155 A | White 155 D |
| Growth rate | Moderate | Vigorous |

I claim:

1. A new and distinct variety of chrysanthemum plant as described and illustrated.

* * * * *